United States Patent [19]

Kefford

[11] Patent Number: 5,308,868
[45] Date of Patent: May 3, 1994

[54] TEAT DIP

[76] Inventor: Bruce Kefford, RMB 3085 Rule Road, Lardner, Vic 3820, Australia

[21] Appl. No.: 949,368

[22] Filed: Sep. 23, 1992

Related U.S. Application Data

[63] Continuation of Ser. No. 585,087, Sep. 21, 1990, abandoned.

[30] Foreign Application Priority Data

Mar. 21, 1989 [AU] Australia ............... PI7342

[51] Int. Cl.$^5$ ............................ A61K 31/20
[52] U.S. Cl. .................. 514/560; 514/947; 514/970
[58] Field of Search ............ 514/560, 947, 970

[56] References Cited

FOREIGN PATENT DOCUMENTS 0243145 10/1987 European Pat. Off. .
939004 6/1982 U.S.S.R. .

OTHER PUBLICATIONS

Chemical Abstracts (96:183537e) 1982.
Chemical Abstracts (97:188302e) 1982.
Chemical Abstracts (108:44061y) 1988.

Primary Examiner—Frederick E. Waddell
Assistant Examiner—K. Weddington
Attorney, Agent, or Firm—Cushman, Darby & Cushman

[57] ABSTRACT

A teat dip composition useful for the treatment of mastitis in dairy cows. The composition in application form is in the form of an oil-in-water emulsion. The oil phase includes an unsaturated fatty acid, for example linseed oil fatty acid, having a carbon chan length in the range of C16 to C20.

7 Claims, No Drawings

TEAT DIP

This is a continuation of application No. 07/585,087, filed on Sep. 21, 1990, which was abandoned upon the filing hereof.

This invention relates to animal health care products and in particular to a teat dip for dairy cows.

The spread of bacterial infection from cow teats during the milking operation results in the spread of the infectious mammary disease known as mastitis. The spread of this disease is usually reduced by the use of known bacteriocides such as chlorine and iodine based compositions. These compositions are usually administered to the teat after removal of the milking cup by dipping or spraying the teat. It is believed these bacteriocides kill a substantial number of bacteria including mastitis pathogens, and thus reduce the spread of bacteria into the mammary gland where mastitis may become evident. There are usually insignificant residual effects of these bacteriocides between milkings. There are problems with the use of these agents including irritation to the teat and teat cracking. To alleviate these problems, emollient additives such as glycerine may be included in these compositions. However, even with the use of these emollients skin irritation can still occur.

It is an object of the present invention to provide a teat dip composition which alleviates some of the problems of the prior art teat dips or to provide at least an alternative teat dip composition.

Accordingly this invention provides in one form a teat dip composition comprising an oil-in-water emulsion wherein the oil phase comprises an unsaturated fatty acid having a carbon chain length in the range C16 to C20.

Preferably the fatty acid has a chain length C18 and more preferably the fatty acid is linolenic acid.

Preferably the composition includes stabilising amounts of surfactants to enable a stable oil-in-water emulsion to be formed. Preferably the surfactants include a non-ionic surfactant, in particular a polyethylene oxide derivative. Most preferably the surfactants are substantially non-ionic. Examples of suitable surfactants are sorbitan monolaurate and ethoxylates thereof. Surfactants are selected on the basis of their ability to form stable oil-in-water emulsions. Generally it is best if at least two surfactants are used, one with a HLB value less than 10 and one with a HLB value in excess of 10. It is important that the surfactants when used in the teat dip composition do not result in unacceptable residues in milk. The surfactants are used at art recognised levels and are typically of the order 1-20% by weight of oil phase. It is believed the surfactants also inhibit the adhesion of mastitis pathogens thereby improving the efficacy of the composition.

The pH of the composition is such that in use irritation to the teat is minimal and a pH in the range 6-8 is found to be particularly suitable.

The relative ratios of oil to water phases are not critical to the working of the composition although from a cost effectiveness viewpoint an oil-in-water ratio in the range of 1/5 to 1/25 is found to be useful in practice. Of course the composition could be packaged for sale at a higher oil-in-water ratio and diluted before use by the dairy farmer by the addition of water. Though this can cause some emulsion stability problems where water quality is poor. Preferably deionised water is used in the compositions of the present invention. Though less preferred it is possible to sell the oil phase which is emulsified before use by the customer.

The fatty acids suitable for the compositions of the present invention can be selected from fatty acids derived from naturally occurring tri-glyceride oils such as vegetable oils, for example, linseed, perilla, soya and safflower. Synthetic unsaturated fatty acids may also be used. One particularly suitable active fatty acid is hydrolysed linseed oil. It will be appreciated that with both the synthetic and natural fatty acids, significant range of compositions of fatty acids can occur. Significant proportions of saturated fatty acid may be present. These are not unduly detrimental to the composition, other than diminishing the level of active unsaturated fatty acid in a given oil phase. The unsaturated fatty acid may be selected, for example, from lauroleic, myristoleic, palmitoleic, oleic, ricinoleic, gadoleic, eruеic. Preferably the level of unsaturation is (—4H) or (—6H) such as in linoleic, linolenic, eleostearic, licanic and arachidic. Preferably at least 20% by weight of the oil phase is unsaturated fatty acid and more preferably at least 30%.

Compositions of the present invention are found to be effective in reducing the spread of mastitis within a herd of dairy cows and at the same time not increasing teat cracking. It is also noted that residues from the present compositions, in particular unsaturated fatty acids, which may ultimately be introduced into milk are believed to be non-harmful and indeed may be already present at low levels in milk. The present compositions also have a residual effect between milkings that is greater than the prior art compositions.

Other ingredients may be used in the composition such as glycerol. This may be present when hydrolysed vegetable oil is used.

Whilst the exact mechanism by which the present composition is effective is unknown it is believed the unsaturated fatty acid is effective in killing the Staphylococus aureus and Streptococci gram positive bacteria) believed to contribute to mastitis disease control by post milking hygiene. Other bacteria particularly gram negative bacteria are relatively unaffected. Thus some bacterial resistance remains from the unkilled bacteria. For example, harmless bacteria remain as a protective coating on the teats. This contrasts to the prior art compositions which essentially kill all bacteria. Hence the compositions of the present invention provides some residual bacterial protection between milkings.

The invention will be further described by references to a preferred embodiment in the following Example in which all parts are parts by weight.

Example 1

A teat dip composition was prepared by dissolving:

| | |
|---|---|
| hydrolysed linseed oil fatty acid | 5 |
| Tween 20* | 1 |
| Span 60** | 1 |

*Tween 20 is a polyethylene oxide sorbitan monolaurate, a non-ionic surfactant of HLB 16.7 manufactured by ICI Speciality Chemical Industries N.V. Approximately 20 ethylene oxide units are condensed onto the sorbitan.
**Span 60 is sorbitan monostearate, a non-ionic surfactant of HLB 4.7 manufactured by ICI Speciality Chemical Industries N. V.

Span 60 is added to the hydrolysed linseed oil, heated and stirred until the Span 60 is dissolved, the Tween 20 is then added to this solution after which this mixture is added to an equal volume of deionised water and agitated. An emulsion formed which was then diluted with more deionised water to lead to 93 parts of water in the overall composition. The resulting teat dip composition was stable over a period of several weeks with no evidence of the emulsion breaking. The composition was evaluated in vitro by appropriate cell counts of S-aureus bacteria. As controls water, chlorine and an iodine based commercial treatments were used. Generally the results showed the composition to be more effective in killing the bacteria than either of the commercial control materials.

In-vitro testing of the Composition of Example 1

Additives at various concentrations were added to molten nutrient agar or Todd-Hewitt agar (for growth of the streptococci) and plates were poured. Cultures of Staphylococcus aureus (15 strains from bovine mastitis cases) and Streptococcus agalactiae (4 strains from bovine mastitis cases) were spotted onto the plates and these were examined for growth after 24h at 27° C.

| Additive | Conc. (ug/ml) at which no growth was seen on agar plates | |
| --- | --- | --- |
| | Staphylococcus aureus | Streotococcus agalactiae |
| Untreated | >660 | >660 |
| Active (LSO)* | | |
| Active (HLSO)** | 330–600 | <66 |
| Example 1 | 330–660 | <66 |
| Surfactants (Tween 20) | >660 | >660 |
| Surfactants (Span 60) | >660 | >660 |

In these tests, as in all others, the strains of Streptococcus agalactiae were much more sensitive to the active ingredient and Example 1 than the strains of Staphylococcus aureus.
*Linseed Oil (LSO)
**Hydrolysed Linseed oil fatty acids (HLSO)

In vivo testing for intra-mammary infections showed that incidence of new infections (in a herd of 75 cows determined by bacteriological culture of mastitis pathogens in milk) was significantly less with the composition of the present invention. It was also noted that teat cracking was minimal and that the general condition of the teats was very good.

Bacteriocidal Efficiency

A teat dip should prove effective in reducing the recoverable number of bacteria (mastitis pathogens) which have been experimentally applied to the teat.

This experiment involved:
a. The application of a mastitis pathogen (Staphylococus aureus) at a concentration of approximately 5×10 CFU/ml to the teats of 10 cows.
b. One front teat and one rear teat of each cow was treated with the teat dip composition.
c. Untreated teats remained as controls.
d. The number of colony forming units of the pathogen recovered by swabbing and culture procedures was compared with the number recovered from control teats.

TABLE 1

| Effect of teat treatment on bacterial count | |
| --- | --- |
| Treatment | Mean log $_{10}$ decrease in bacterial numbers |
| Composition of Example 1 | 3.15 |
| Iodine (5,000 ppm) | 1.68 |

TABLE 1-continued

| Effect of teat treatment on bacterial count | |
| --- | --- |
| Treatment | Mean log $_{10}$ decrease in bacterial numbers |
| Hibitane (Chlorhexidine) | 1.51 |

According to the Draft Standards an "effective" bacteriocide should decrease the number of bacteria recovered by log $_{10}$ 1.7 (or 98% kill).

These results show the composition of the present invention is very bacteriocidally efficient and much more efficient than the two prior art teat dips.

Teat Condition

This evaluation involved:
a. The application of the teat dip to one front teat and one hind teat at each milking.
b. The remaining teats were untreated or dipped in a registered teat dip.
c. Teats are scored with respect to chaps, sores and skin condition at fortnightly intervals.
d. Comparison of control and test teat scores were made with respect to:
  (i) total number of chaps;
  (ii) total number of teat sores;
  (iii) total teat lesions (i.e. chaps plus sores;
  (iv) numbers of rough skinned teats.

Results

Two herds tested in Autumn (when teat condition is relatively good) showed no significant difference between scores treated with the composition according to the invention and the scores of iodine (5000 ppm) or treated teats. There is no deleterious effect of the composition of the present invention. It is also possible that a positive improvement in teat condition with the composition may be seen when the general level of teat condition is poorer, say in Winter.

Non-contamination of milk

The use of the teat dip should not impart flavour, odour or colour to milk or milk products or introduce harmful concentrations of residues.

Results a. Residues.

It is difficult to test residues of the composition using the standard procedures as there are quantities of the active ingredient in the lipids of normal milk. An estimate of the quantity of this component that could be added to the milk during milking i.e. say 10% of the teat dip is transferred to the milk) indicates that any residue is far outweighed by the natural levels of this compound in the milk lipids.

Estimates (i) Contribution of active ingredient to milk = 0.25 mg/100 ml.
NOTE: This level of the compound is too low to detect using current technology.
(ii) Content of active ingredient in normal milk = 20 mg/100 ml.

In addition, as the other components of the teat dip are FOOD GRADE chemicals at a lower concentration than the active compound it seems very unlikely that these compounds could significantly contaminate the milk under normal conditions.

b. Toxicity for Cheese Starters and Yoghurt makers

The composition of Example 1 was tested at the Gilbert Chandler Institute of Dairy Technology, Werribee, for its effect on cheese starter and yoghurt making bacteria. The effect of test compounds on these bacteria is measured in terms of the change in pH during the cheese yoghurt making. If the cheese containing a test compound, at a given concentration, has a pH at the end of the incubation >0.2 units higher than the control batch then the test compound had a significant effect at that concentration. It was found with the composition of Example 1 that at concentrations <1 ul/ml of milk there was no significant effect on cheese or yoghurt making.

This concentration (1 ul composition of Example 1/ml of milk) represents a dilution of 1:1000. For a cow yielding 20 liters of milk 20 ml of composition of Example 1 would be required to significantly affect cheese and yoghurt making. As approximately 10–15 ml of teat dip is used per cow, some drains off and some would be removed during the pre-milking washing, it is unlikely that under normal milking conditions such a level of contamination could be achieved.

Residual Effects

When the composition of Example 1 was tested on the two herds for its effect on teat skin, swabs were also taken of the teats that had been treated twice daily with either the composition of Example 1, iodine (5000 ppm) or untreated for 8 weeks. At the end of the experiment swabs of all teats were taken 14 hours after treatment and serial dilutions of fluid from them were plated onto staphylococcal selective medium sheep blood agar).

Two bacterial types grew on the selective medium staphylococci and bacilli) whereas a range of colony types including the above were seen on the non-selective plates ("total" bacteria).

Results Swabs from the composition of Example 1 treated teats when compared to iodine-treated teats have:

| | | |
|---|---|---|
| 2.8 times fewer staphylococci | ) | selective |
| 1.5 times more bacilli | ) | medium |
| and | | |
| 1.5 times fewer "total" bacteria | ) | non-selective medium |

Swabs from the composition of Example 1 treated teats when compared with untreated teats have:
4.6 times fewer staphylococci
1.4 times more bacilli
and
4.5 times fewer "total" bacteria
These results suggest:
(i) The composition of Example 1 is more effective than iodine in holding staphylococcal numbers down between milkings.
(ii) The composition of Example 1 promotes the survival of bacilli (and possibly other less pathogenic bacteria on teats which may lead to reduced reinfection of the teat through competition.
(iii) Composition of Example 1 reduced the "total" population of bacteria on teats.

Since modifications within the spirit and scope of the invention may be readily effected by persons skilled in the art, it is to be understood that the invention is not limited to the particular embodiment described, by way of example, hereinabove.

Dated this 20th day of March 1989.

DARATECH PROPRIETARY LIMITED
PATENT ATTORNEY FOR THE
APPLICANT: DAVID GIBSON

I claim:

1. A method of reducing the effects of mastitis in cows which comprises applying to the teats of the cow an amount of a composition consisting essentially of an oil-in-water emulsion of linseed oil fatty acid as the active ingredient and a stabilizing amount of an essentially non-ionic surfactant.

2. A method as defined in claim 1 wherein in said composition said linseed oil fatty acid is present in an amount of at least 20% by weight of the oil phase.

3. A method as defined in claim 1, wherein in said composition said active ingredient is hydrolyzed linseed oil.

4. A method as defined in claim 1, wherein said composition further includes glycerol.

5. A method as defined in claim 4, wherein said glycerol is present in an amount over 10% w/w of the fatty acid content.

6. A method as defined in claim 1, wherein in said composition said non-ionic surfactant is present in an amount of between 1 and 20% by weight of the oil phase.

7. A method as defined in claim 1, wherein in said composition there are at least two surfactants one with HLB less than 10 and one with HLB greater than 10.

* * * * *